(12) United States Patent
Revie et al.

(10) Patent No.: US 6,893,445 B1
(45) Date of Patent: May 17, 2005

(54) PRESSURIZER DEVICE

(76) Inventors: Ian Revie, Tutt House, New Row, Boroughbridge (GB) Y051 9AW; John Naybour, 2-Pen-y-lon, Mynydd Isa, Mold, Flintshire (GB)

(\*) Notice: Subject to any disclaimer, the term of this patent is extended or adjusted under 35 U.S.C. 154(b) by 84 days.

(21) Appl. No.: 09/946,924

(22) Filed: Sep. 5, 2001

Related U.S. Application Data

(63) Continuation-in-part of application No. 09/385,669, filed on Aug. 27, 1999, now abandoned.

(51) Int. Cl.[7] .............................................. A61B 17/58
(52) U.S. Cl. ........................................ 606/94; 606/86
(58) Field of Search .............................. 606/94, 95, 92, 606/93, 86; 623/23.48, 23.46, 23.21, 23.22, 623/22.12, 23.19, 23.37; 433/173; 206/63.5

(56) References Cited

U.S. PATENT DOCUMENTS

| | | | |
|---|---|---|---|
| 4,128,454 A | 12/1978 | Schleinkofer | |
| 4,366,901 A * | 1/1983 | Short | 206/210 |
| 4,815,454 A | 3/1989 | Dozier, Jr. | |
| 4,827,919 A | 5/1989 | Barbarito et al. | |
| 4,997,448 A * | 3/1991 | Filer | 623/23.2 |
| 5,290,524 A | 3/1994 | Rosenblatt et al. | |
| 5,507,749 A * | 4/1996 | Draenert | 606/94 |
| 5,741,265 A * | 4/1998 | Chan | 606/94 |
| 5,766,262 A | 6/1998 | Mikhail | |
| 5,819,341 A * | 10/1998 | Simantob et al. | 5/98.1 |
| 6,017,350 A * | 1/2000 | Long | 606/94 |
| 6,254,641 B1 * | 7/2001 | Revie et al. | 623/23.48 |

FOREIGN PATENT DOCUMENTS

| | | |
|---|---|---|
| EP | 0320138 B1 | 6/1989 |
| EP | 0448390 A2 | 9/1991 |
| WO | WO 86/04698 | 8/1986 |
| WO | WO9000375 | 1/1990 |

\* cited by examiner

Primary Examiner—Pedro Philogene

(57) ABSTRACT

A pressurizer device (1) is provided for maintaining pressure in the cement in a bone cavity during introduction of a prosthetic component, for example, a replacement hip stem. The pressurizer device (1) has a collar (4) and a hood (3). The hood (3) has a hoop (20) which arches across the central opening (14) of the collar (4). The hood (3) can be provided with or without a lining.

8 Claims, 13 Drawing Sheets

PRESSURIZER DEVICE

CROSS REFERENCE TO RELATED APPLIACTIONS

This application is a Continuation-in-Part of U.S. patent application Ser. No. 09/385,669 filed Aug. 27, 1999, now abandoned, entitled PRESSURIZER DEVICE.

TECHNICAL FIELD OF THE INVENTION

The present invention relates generally to the field of orthopaedics, and more particularly to a pressurizer device for use in cemented femoral hip stem replacement. The pressurizer device is also suitable for use in other cemented prosthetic applications.

BACKGROUND OF THE INVENTION

This invention relates to implantable articles and methods for manufacturing such articles. More particularly, the invention relates to bone prosthesis and process for manufacturing the same.

There are known to exist many designs for and methods for manufacturing implantable articles, such as bone prostheses. Such bone prostheses include components of artificial joints, such as elbows, hips, knees and shoulders.

A femoral bone is prepared for replacement hip stem prosthesis by expanding the internal cavity of the femoral bone by using a broach or rasp. The broached cavity is filled with bone cement either before or after the insertion of the hip stem prosthesis.

An important consideration in the design and manufacture of virtually any implantable bone prosthesis is that the bone prosthesis has adequate fixation when implanted within the body.

Early designs of implantable articles have relied upon the use of cements such as polymethylmethacrylate (PMMA) to anchor the implant. The use of such cements can have some advantages, such as providing a fixation that does not develop free play or does not lead to erosion of the joining faces postoperatively.

In the method in which a hip stem prosthesis is inserted after the cement is introduced into the broached cavity, it is important to centralise the stem within the prepared femoral cavity and to maintain the pressure of the cement surrounding the hip stem prosthesis. Centralisation of a hip stem prosthesis and pressurisation of the cement have been linked to long term stem survivability in hip replacement surgery. Loss of pressure of the cement may permit blood to displace some of the cement within the broached cavity.

Known pressurizer devices are either removed prior to stem introduction or a part of the pressurizer is removed or changed to a separate component thereby disturbing the cement and the pressure generation. It is an object of the present invention to maintain the pressure on the cement with little or no disturbance.

SUMMARY OF THE INVENTION

According to the present invention, there is provided a pressurizer device having a collar defining an opening for accommodating a prosthetic component, and a hood attached to the collar which can enclose at least a portion of the central opening of the collar.

Preferably, the hood is moveable between two positions, a first position in which the hood covers at least a portion of the opening and a second position in which the opening is uncovered. The hood may be in the first position when cement is being inserted into the medullary canal or when the prosthesis is in position in the canal. The opening may be uncovered during the insertion of the prosthesis.

Preferably, the collar has an outer surface corresponding to the shape of a bone cavity in which the prosthetic component is to be inserted.

Preferably, the hood has a hoop extending across the opening in the collar. Preferably, a covering of the hood extends from the hoop to the collar.

Preferably, the hoop conforms to the shape of the prosthetic component. The hoop may be attached to the collar, for example, by being integrally molded with the collar or by being inserted into a mold and the collar being molded into the hoop. The hoop may thus be moveable from a first relaxed vertical position to a second restrained position in which the hoop is folded laterally.

Optimally, the body of the hood corresponds to the shape of the prosthetic component to be inserted. The hood may be attached to the collar along the anterior and posterior aspects of the collar.

Preferably, the hood is attached to the collar by a tearable and flexible membrane. The collar may be integrally molded with the hood and the membrane may be perforated or have a reduced thickness compared to the hood.

The hood may be lined with an insert to stiffen the hood. The insert may also conform to the shape of the prosthetic component and may be made of polyethylene.

According to one embodiment of the present invention, there is provided a pressurizer device having a collar defining an opening for accommodating a prosthetic component, and a moveable hood attached to the collar which can be positioned to enclose at least a portion of the central opening of the collar.

According to another embodiment of the present invention there is provided a sealing device for cooperation with a resected long bone. The device is adapted to have a first configuration for providing a seal between the resected long bone and cement dispensing device and a second configuration for providing a seal between the resected long bone and a prosthesis component.

According to yet another embodiment of the present invention there is provided a sealing device for providing a seal between a resected long bone and a cement dispensing device during the dispensing and pressurizer of cement during implantation of a prosthesis. The sealing device is adapted to permit the portion of the sealing device in contact with the resected long bone to remain in such contact during the insertion of a prosthesis component into the resected long bone.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
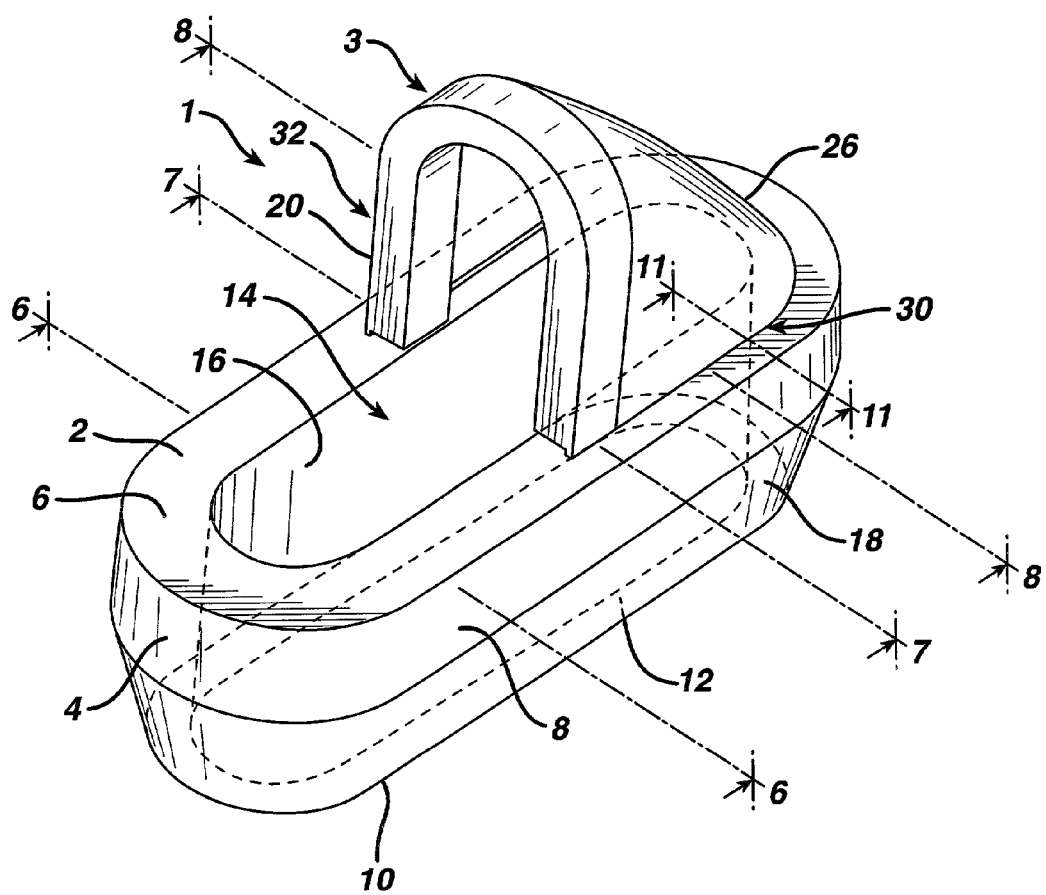
FIG. 1 is a perspective view of a pressurizer device in accordance with the present invention showing the hood in a first position.

According to the present invention and referring now to FIG. 1, a pressurizer device 1 is provided. The pressurizer device 1 is formed in two parts. A collar 4 and a hood 3. The collar 4 and the hood 3 are preferably made of a suitable, durable and flexible material. For example, the collar 4 may be formed of a silicone, for example, a medical grade silicone. Likewise, the hood 3 may be formed of a silicone, for example a medical grade silicone. While the pressurizer device 1 may be made by any suitable manufacturing techniques, preferably the collar 4 and the hood 3 of the pressurizer device 1 may be integrally molded in an injection molding machine and made from a medical grade silicone.

Preferably and as shown in FIG. 1, the body 2 of the pressurizer device 1 is in the form of a collar 4. The collar 4 has a top surface 6, sides 8 and a bottom surface 12.

As shown in FIG. 1, the collar 4, the sides 8 form a central opening 14. The central opening 14 of the collar preferably corresponds to the shape of the prosthetic component. The pressurizer device 1 of the present invention is suitable for use with any component including a stem which fits into a cavity formed in a medullary canal of a long bone. For example, the invention may be suited for the femoral component of a hip prosthesis, the tibial component of a knee prosthesis, the femoral component of a knee prosthesis or the humeral component of a shoulder prosthesis. For example and as shown in FIG. 1, the pressurizer device 1 is suited for a hip stem to be positioned in a femoral component of a hip prosthesis. The central opening 14 of the collar 4 corresponds to the shape of the hip stem. The opening 14 has internal walls 16 that fit the proximal section of a hip stem.

The body 2 has a lower section 10 with external walls 18. The external walls 18 of the lower section 10 correspond to a broach femoral canal in which the pressurizer device is inserted such that the body 2 sits in the entry to the broach canal of the patient's bone.

The pressurizer device 1 preferably has a hood 3 with a hoop 20 that extends in an arch across the opening 14 of the collar 4. Since the opening 14 of the collar 4 corresponds to a proximal section of a hip stem, it is generally oval in shape and the hoop 20 extends centrally across the narrow width of the oval shape. The hoop 20 corresponds to the hip stem shape.

As the hoop 20 and the hood 3 may be integrally molded with each other and may be made of a flexible material, the pressurizer device 1 may provide for the hoop 20 to have a first position as shown in FIG. 1 in solid with the hoop 20 being in a substantially vertical direction and a second position (see FIG. 3) in which the hoop 20 is in a substantially horizontal position. The flexible hood thus provides for the hoop 20 to have movable positions from the position in FIG. 1 to the position in FIG. 3. Thus it may be considered that the hoop 20 operates with respect to the pressurizer device as though it were hinged or on a "sprung hinge". The sprung hinge 22 attaches the hoop 20 to the collar 4. The hoop 20 folds laterally against the spring hinge 22 (see FIG. 3).

The hood 3 may alternately be lined with an insert or hood lining not shown. The hood lining 24 may assist in stem introduction by stiffening the hood and allowing the stem to be introduced easily. The hood lining may be in the form of a polyethylene insert. The insert may be molded with the pressurising device or assembled into the pressurising device. The insert may be thick enough to be somewhat rigid and if made of polyethylene may be, for example, from 1 to 2 mm thick.

The hood 3 may be attached to the pressurizer device 1 along anterior aspect 30 and posterior aspect 32 of the top surface 6 of the collar 4 by a tearable, flexible membrane 34 which is designed to rip or stretch on opening the hood 3.

Figure 2:
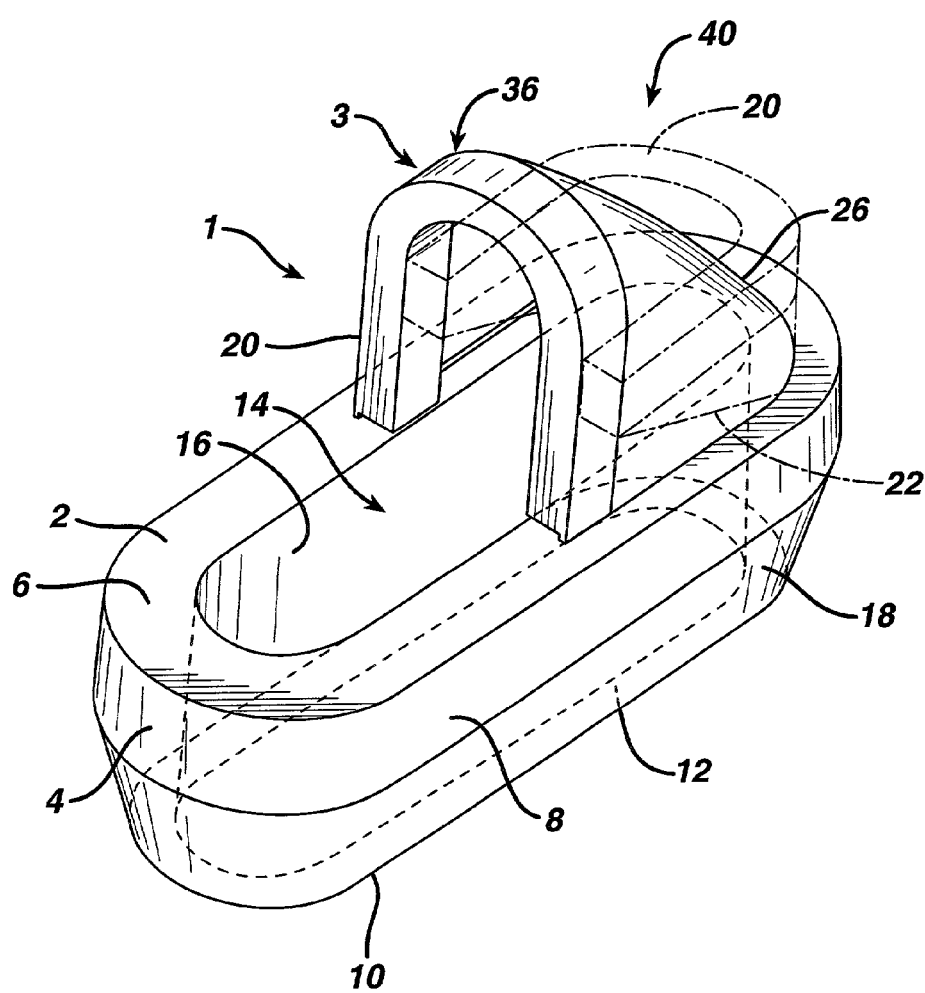
FIG. 2 is a perspective view of the pressurizer device of FIG. 1 showing the hood in both the first positions in solid and in a second position in phantom.

Referring now to FIG. 2, the pressurizer device 1 is shown with the hoop 20 of the hood 3 in first position 36 as shown in solid with the hoop 20 being in a substantially vertical position and a second position 40 as shown in phantom with the hoop 20 being in a substantially horizontal direction. Referring to FIG. 2, it should be appreciated that in first position 36 the hood 3 serves to partially close central opening 14 of the pressurizer device 1. It should also be appreciated that when the hood 3 is in the second position 40, the central opening 14 is substantially uncovered.

Figure 3:
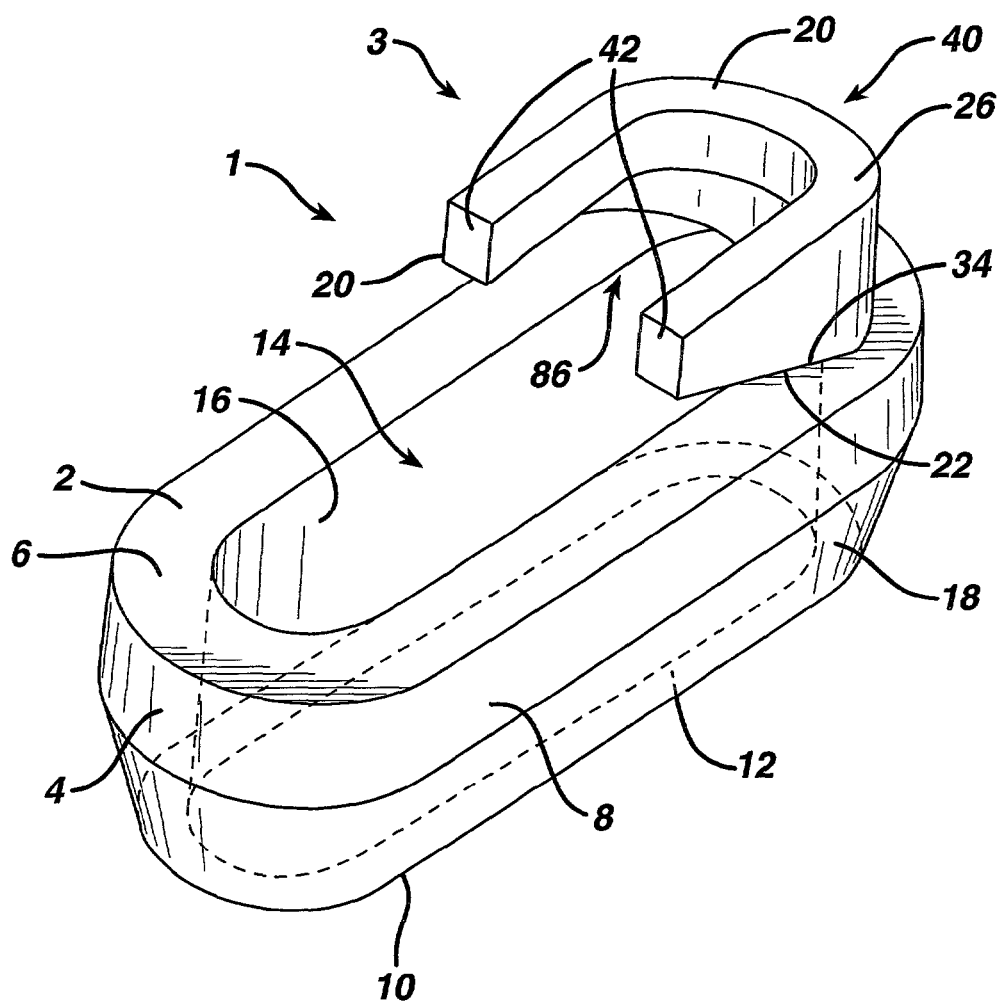
FIG. 3 is a perspective view of the pressurizer device of FIG. 1 showing the hood in the second position.

Referring now to FIG. 3, the second uncovered position 40 of the opening 14 of the pressurizer device 1 is shown more clearly. As shown in FIG. 3, the membrane 34 of the hood 3 is shown in a torn or separated condition from top surface 6 of the collar 4. Preferably and as shown in FIG. 3, the hoop 20 and the collar 4 are not attached at bottom surface 42 of the hoop 20. By having the bottom surfaces 42 of the hoop 20 not connected to top surface 6 of the collar 4, only membrane 34 serves to secure the hood 3 to the collar 4. Thus the thin membrane 34 may be easily torn to move the hood 3 into position 40.

Figure 4:
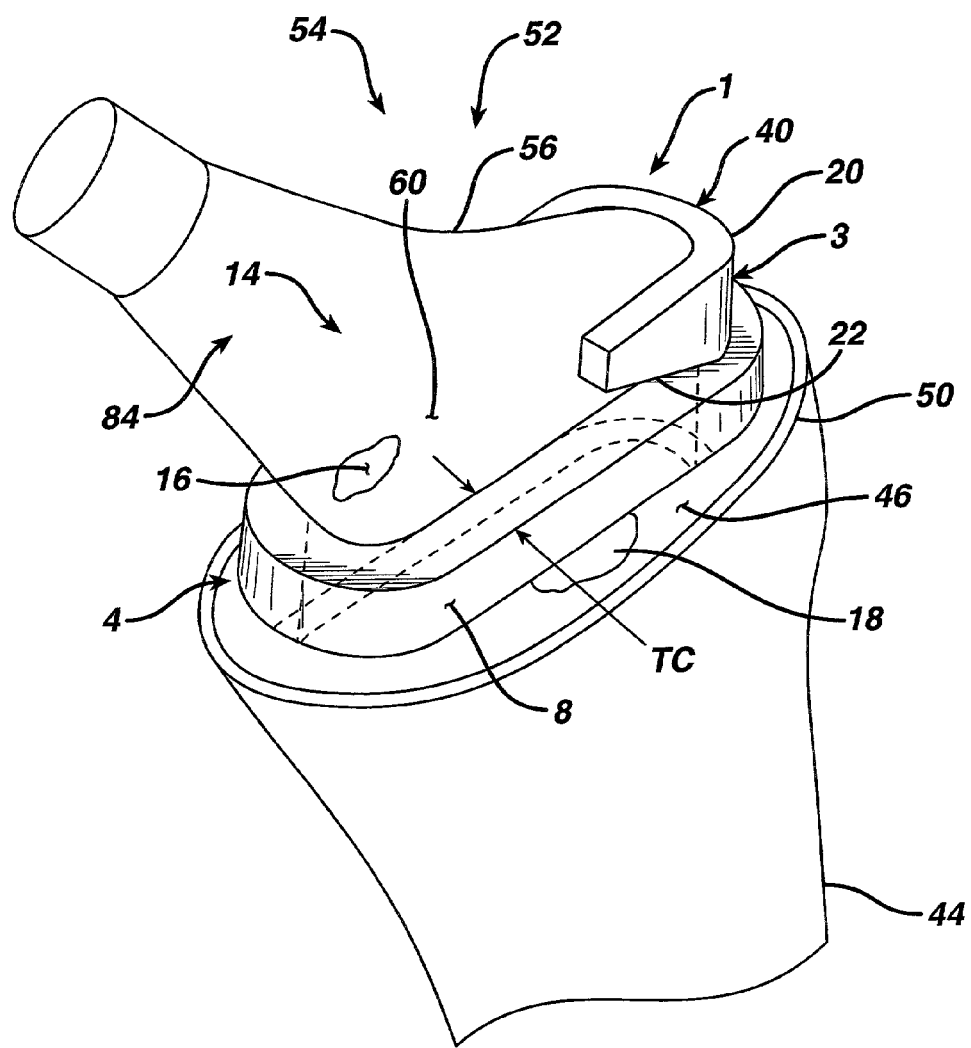
FIG. 4 is a perspective view of the pressurizer device of FIG. 1 showing the pressurizer device in position in a long bone with a prosthesis stem partially inserted into the medullary canal.

Referring now to FIG. 4, the pressurizer device 1 is shown in position secured to long bone 44. Long bone 44 may be, for example, as shown in FIG. 4 a femur. The femur 44 includes cancellous bone 46 and a ring of outer or cortical bone 50 surrounding the cancellous bone 46. Typically an opening 52 is formed in medullary canal 54 of the long bone 44. The exterior walls 18 of the collar 4 of the pressurizer device 1 are preferably designed to conform to the opening 52 formed in the femur 44.

As shown in FIG. 4, a prosthesis 56 in the form of a hip stem is shown partially inserted through opening 14 of the pressurizer device 1 and partially fitted into opening 52 of the medullary canal 54. To permit the prosthesis 56 to fit within the opening 14 of the pressurizer device 14, the hoop 20 is positioned in the open position 40 as shown. The internal walls 16 of the pressurizer device 1 are preferably designed to conform with proximal surfaces 60 of the prosthesis 56.

Figure 5:
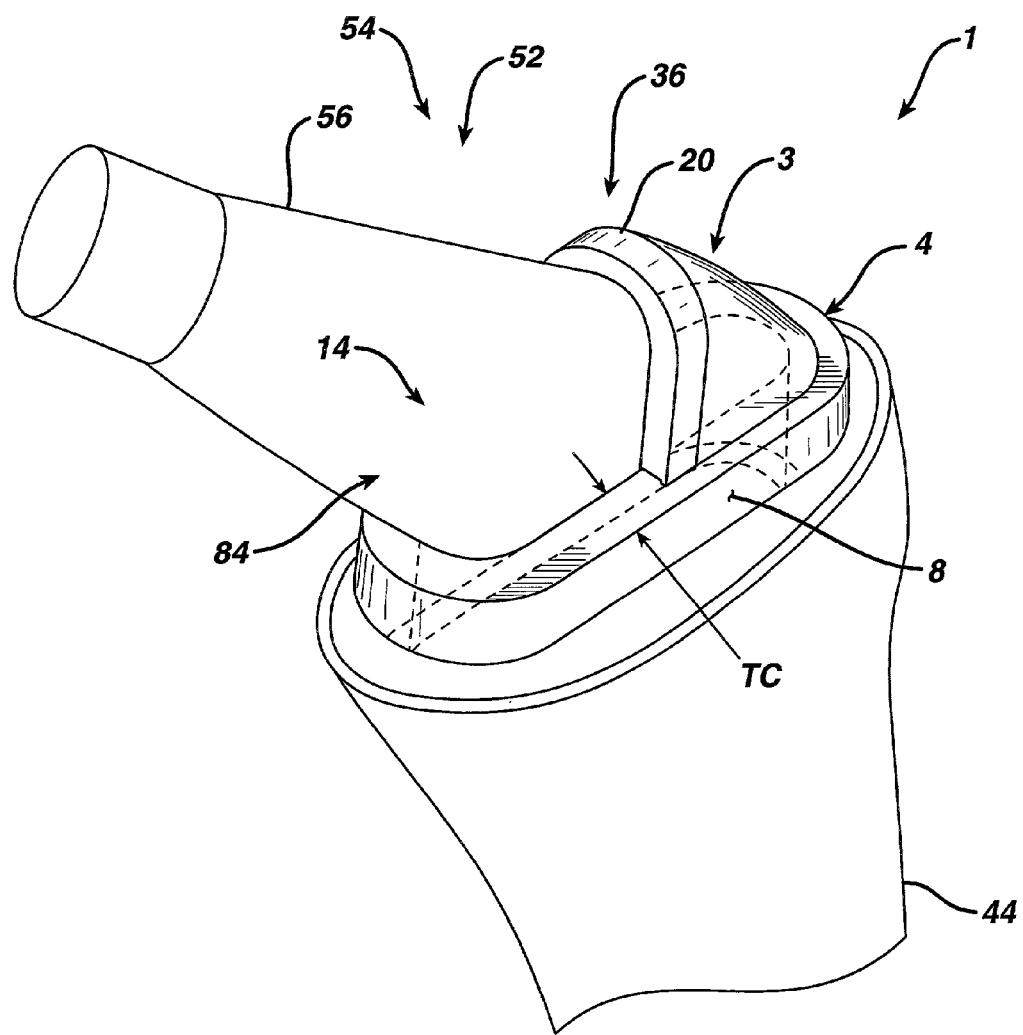
FIG. 5 is a perspective view of the pressurizer device of FIG. 1 showing the pressurizer device in position in a long bone with a prosthesis stem completely inserted into the medullary canal.

Referring now to FIG. 5, the hip stem 56 is shown fully inserted into medullary canal 54 of the femur 44. To fully seal the hip stem 56 when in the fully engaged position as shown in FIG. 5, the hood 3 is shown in first position 36 with the hoop 20 in a generally vertical direction. In this position, the hood 3 partially covers the opening 14 of the pressurizer device 1.

Figure 6:
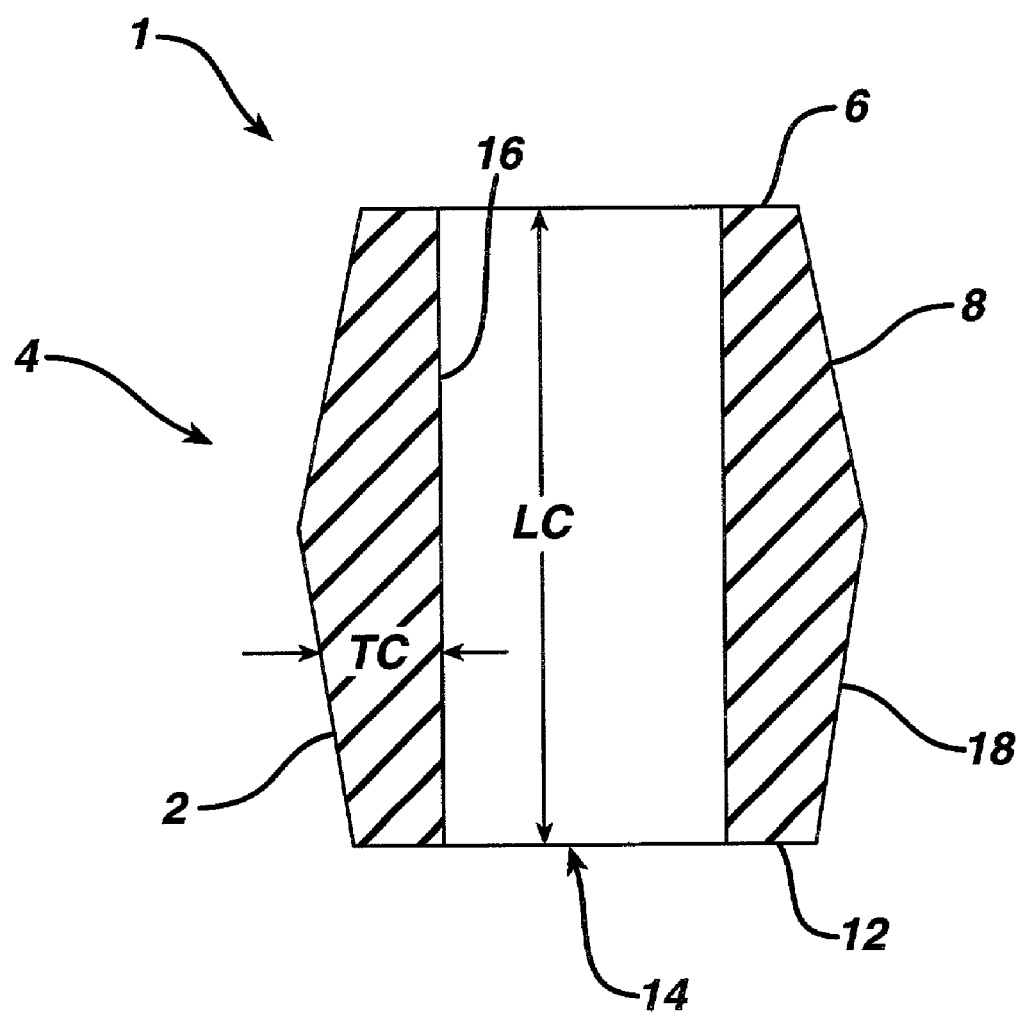
FIG. 6 is a cross sectional view of the pressurizer device of FIG. 1 along the line 6—6 in the direction of the arrows.
Figure 7:
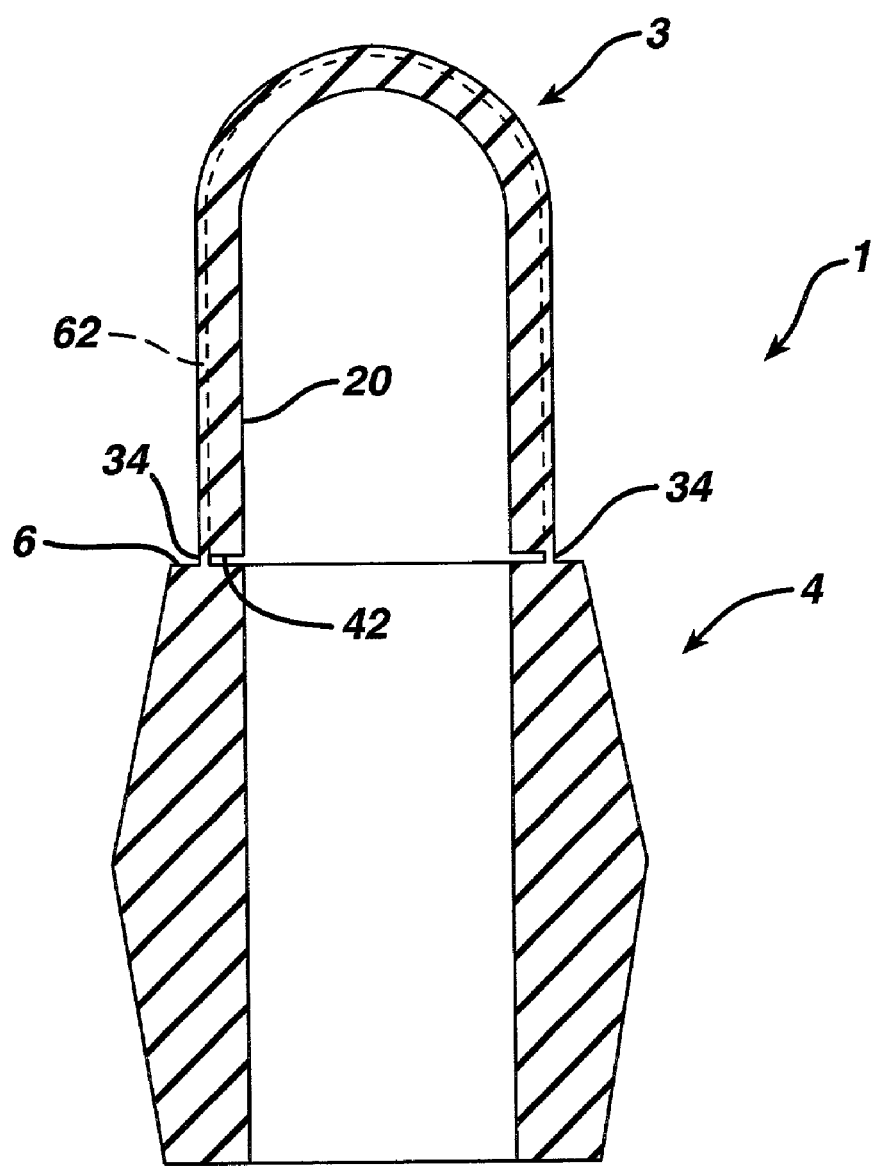
FIG. 7 is a cross sectional view of the pressurizer device of FIG. 1 along the line 7—7 in the direction of the arrows.
Figure 8:
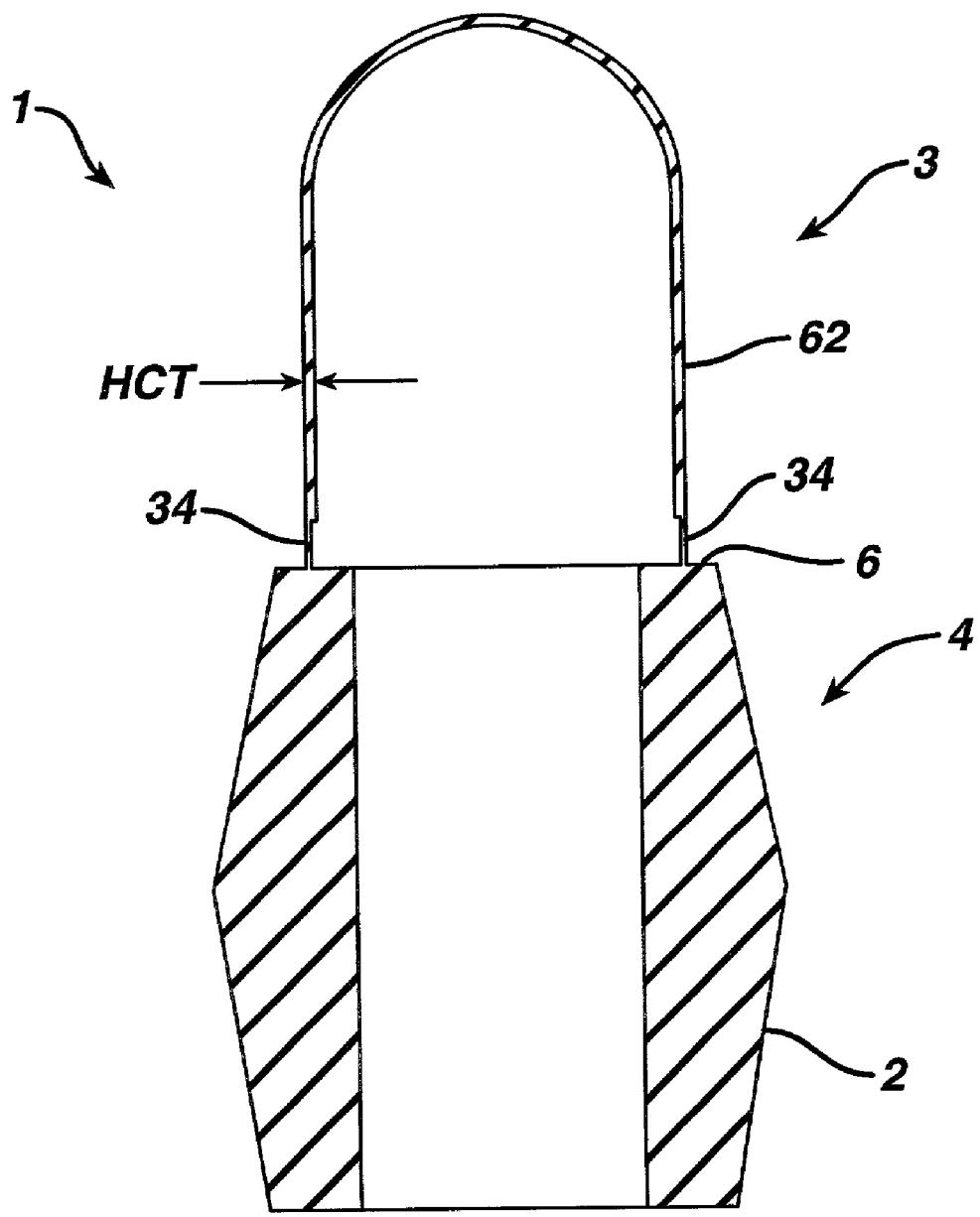
FIG. 8 is a cross sectional view of the pressurizer device of FIG. 1 along the line 8—8 in the direction of the arrows.

Referring now to FIGS. 6, 7 and 8, the pressurizer device 1 is shown in greater detail. Referring now to FIG. 6, the collar 4 is shown in cross-sectional view. As shown in FIG. 6 the collar 4 may have a bottom surface 12 and opposed top surface 6. The collar 4 has a central opening 14. The collar 14 may have a thickness TC which varies from, for example, approximately 10 mm to 15 mm. It should be appreciated that depending on the material used for the collar the thickness TC may vary considerably from that mentioned. The collar 4 may also have a collar length LC extending from top surface 6 to bottom surface 12 of, for example, around 40 mm. It should be appreciated that the collar length LC may vary substantially from 40 mm.

Referring now to FIG. 7, the pressurizer device 1 is shown in cross-section with the collar 4 and the hood 3 as shown. As shown in FIG. 7 the bottom surface 42 of the hoop 20 is spaced from top surface 6 of the collar 4. The hood 3 is thus attached to the collar 4 at the flexible membrane 34. The flexible membrane 34 may thus either stretch or tear so that the hoop 20 may be positioned in the horizontal direction (see FIG. 3). Preferably the hood 3 includes a hood covering 62. The hood covering 62 extends from hoop 20 as well as from top surface 6 of the collar 4. The hood covering 62 may be integral with the hoop 20 and the collar 4.

Referring now to FIG. 8, the hood covering 62 of the pressurizer device 1 is shown in greater detail. The hood covering 62 may have a thickness HCT of, for example, approximately 0.1 to 0.3 mm. It should be appreciated depending on the material from which the hood covering 62 is made that the appropriate thickness of the hood covering may vary.

Figure 11:
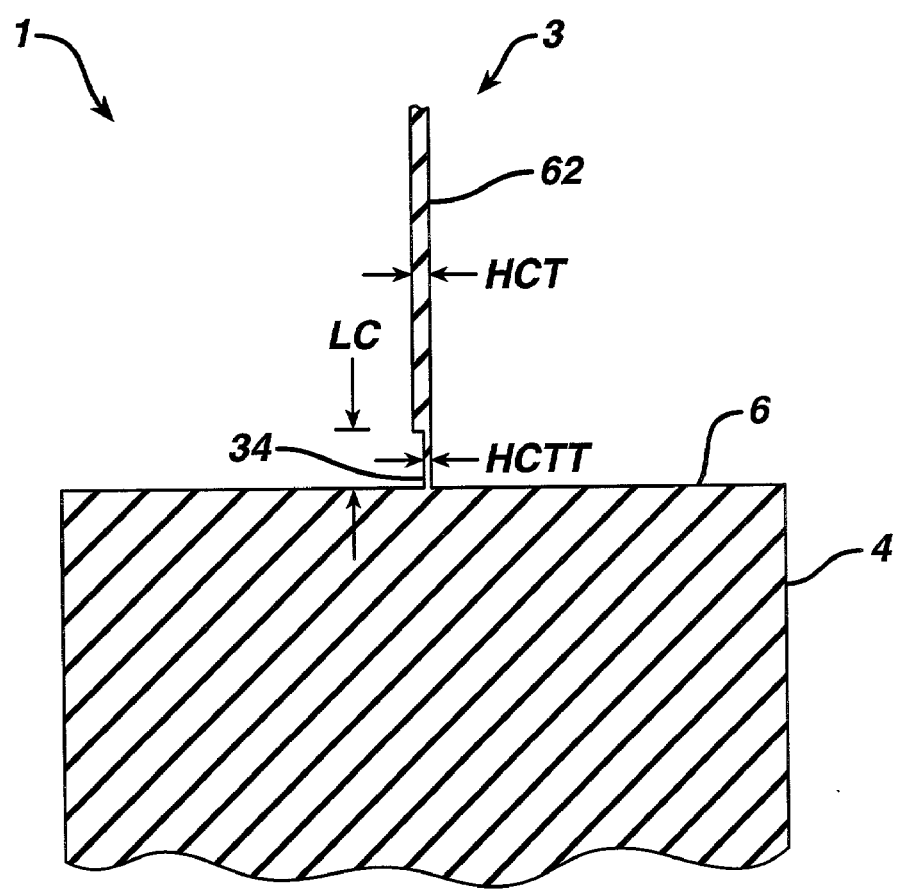
FIG. 11 is a partial cross sectional view of the pressurizer device of FIG. 1 along the line 11—11 in the direction of the arrows.

Referring now to FIG. 11, the tearable flexible membrane 34 of the pressurizer device 1 is shown in greater detail. As shown in FIG. 11, the hood covering 62 includes the tearable flexible membrane 34 extending from top surface 6 of the collar 4. To control the stretch and tearing of the hood covering 62 at the tearable flexible membrane 34, the tearable flexible membrane 34 may, for example, have a reduced thickness HCTT of approximately 0.02 to 0.10 mm. The reduced thickness of the tearable flexible membrane 34 may extend from top surface 6 a distance LC of, for example, 0.1 mm to 0.5 mm.

Figure 12:
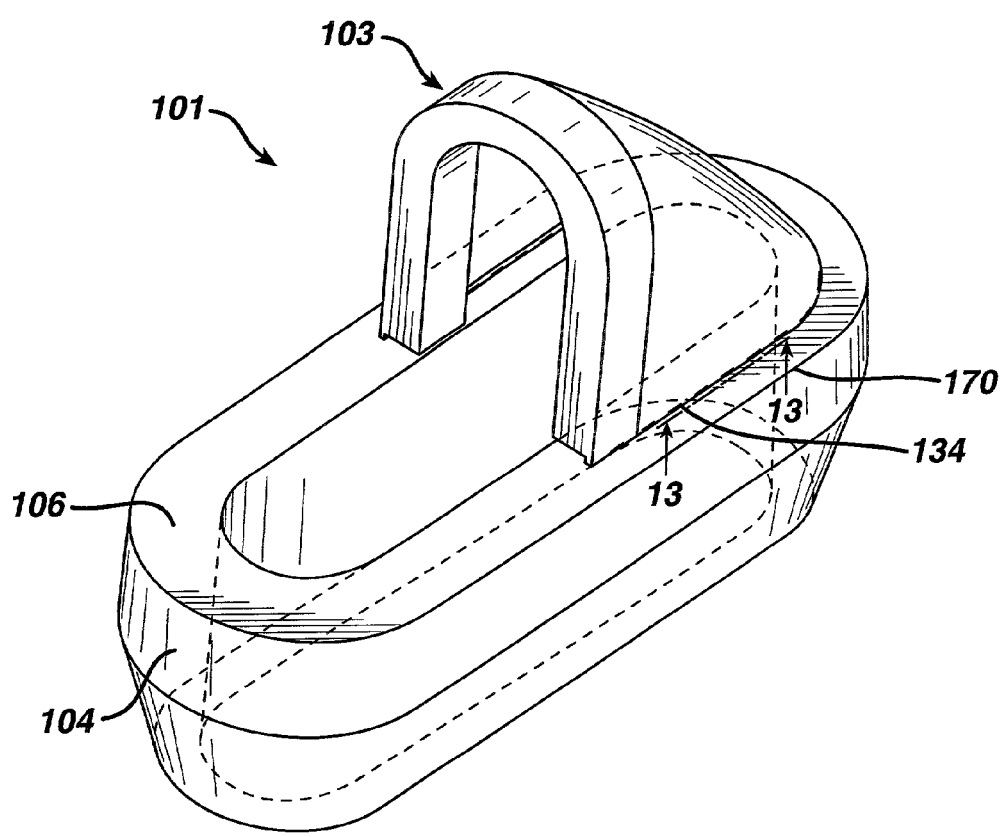
FIG. 12 is a perspective of an alternate embodiment of the pressurizer device of the present invention utilising a perforated sprung hinge.
Figure 13:
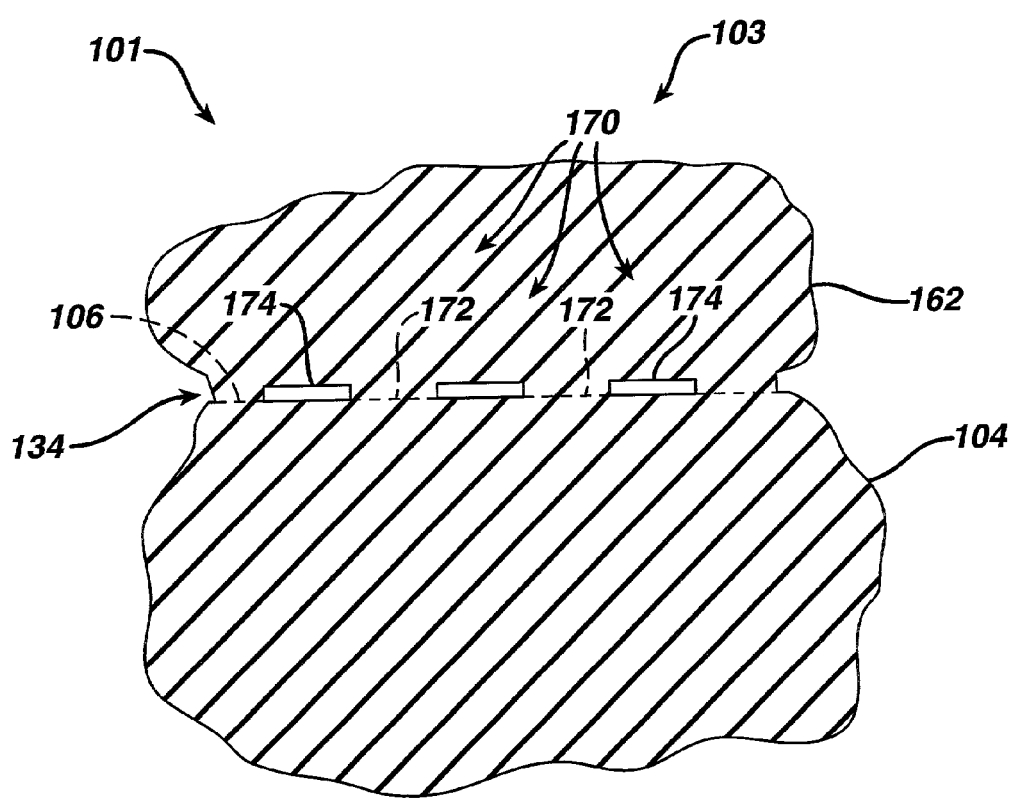
FIG. 13 is a partial cross sectional view of FIG. 12 along the line 13—13 in the direction of the arrows.

Referring now to FIGS. 12 and 13, the pressurizer device according to the present invention may include alternate forms of the tearable flexible membrane. For example, as shown in FIG. 12, pressurizer device 101 is similar to pressurizer device 1 of FIG. 1. The pressurizer device 101 includes a hood 103 similar to hood 3 of the pressurizer device 1 of FIG. 1 and a collar 104 similar to collar 4 of the pressurizer device 1 of FIG. 1. As shown in FIG. 12 the pressurizer device 101 has a tearable flexible membrane 134 which includes perforations 170.

Referring now to FIG. 13, the pressurizer device 103 includes contact portions 172 that attach the hood covering 162 to top surface 106 of the collar 104. Between adjacent contact portions 172 are separation portions 174. The contact portions 172 and the separation portions 174 together form the perforations 170 in the membrane 134 of the hood covering 162. Depending on the thickness and strength of the hood covering 162, the contact portions 172 and the separation portions 174 may have their heights and widths adjusted accordingly.

When implanting a cemented stem prosthesis in, for example, a femur for a hip prosthesis, a tibia or a femur for a knee prosthesis, or a humerus for a shoulder prosthesis, for example, first the long bone is resected or cut off. Next, an opening is formed in the medullary canal of the long bone. The next step is the introduction of cement commonly in the form of polymethylmethacrylate (PMMA). After the PMMA has been introduced into the medullary canal, the prosthetic stem is implanted into the long bone.

The preparation of the opening in the medullary canal of the long bone for utilizing this invention is similar to any current technique now available for preparing the medullary canal including reaming and broaching. Such procedures are well known and will now be described in detail in this disclosure.

Figure 10:
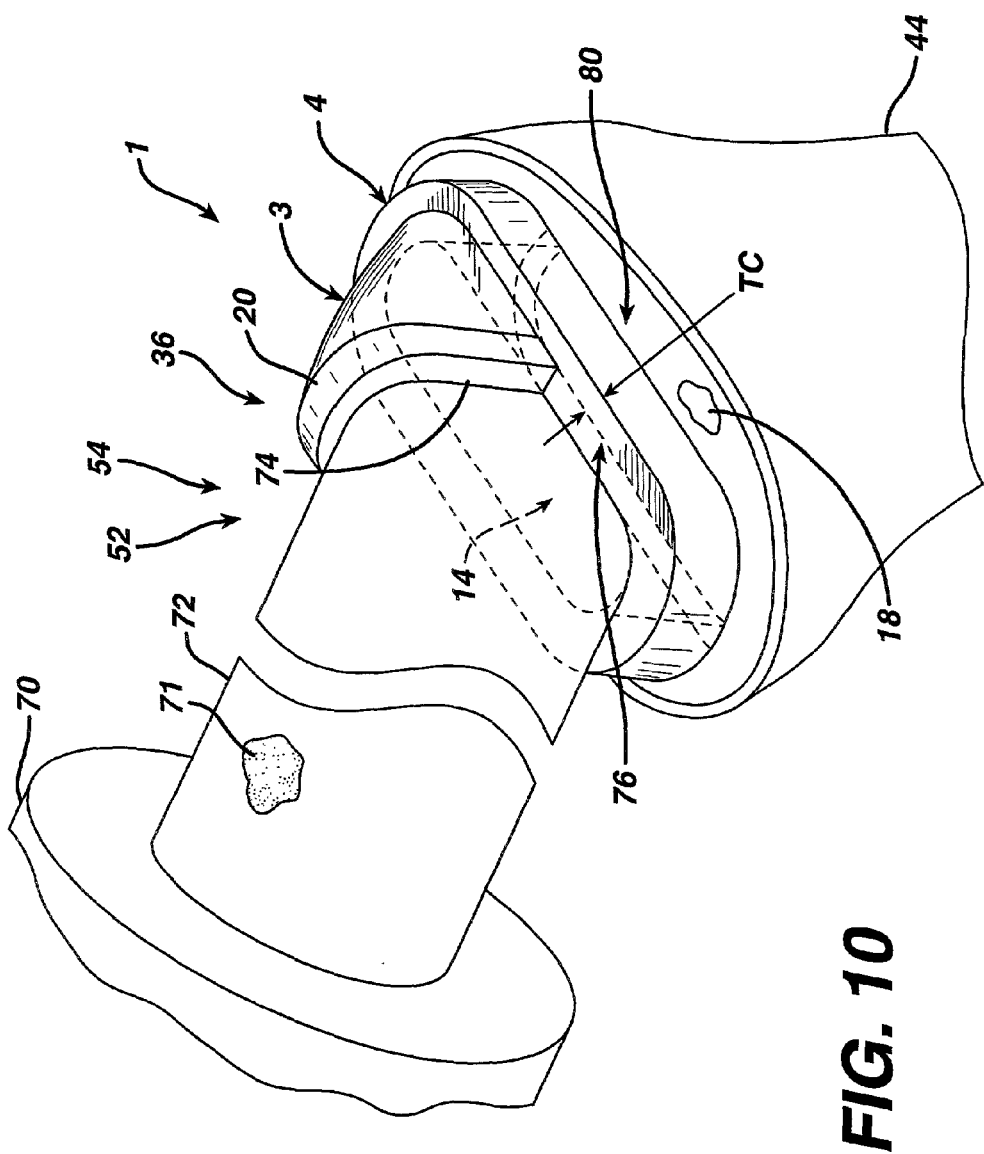
FIG. 10 is a perspective view of the pressurizer device of FIG. 1 showing the pressurizer device in position in a long bone with a cement filling gun nozzle positioned over the opening of the pressurizer device to inject cement within the cavity formed in the medullary canal.

Referring now to FIG. 10, a cement gun or injector 70 is utilized to inject PMMA cement 71 into the opening 52 formed in medullary canal 54 of the femur 44. The cement gun 70 includes a gun nozzle 72 which includes a nozzle tip 74 which conforms to opening 14 of the pressurizer device 1. The tip 74 of the gun nozzle 72 thus forms a first seal 76 between the tip 74 and the pressurizer device 1 while the external walls 18 of the pressurizer device 1 and the opening 52 in the medullary canal 54 form a second seal 80 between the pressurizer device 1 and the long bone 44.

The cement 71 may thus be applied to the opening 52 in the medullary canal 54 under pressure. For example, the cement 71 may have a pressure which is greater than a patient's blood pressure. The pressurisation assures that cement displaces the blood in the opening 52 of the medullary canal 54. The pressurisation of the cement 71 thus serves to assure that the cement 71 completely fills the opening 52 with minimal voids or pockets within the opening 52. Further, if sufficient pressure is applied by the cement gun 70, the cement 71 may penetrate a portion of the cancellous bone 46 of the femur 44. The penetration of cement 71 into the cancellous bone 46 is known as interdigitation and provides improved fixation of the prosthesis.

Referring to FIG. 10, it should be appreciated that the tip 74 may have any of a number of suitable configurations depending on the position of the hood 3. For example the tip 74 may be designed for use with any position from the vertical position 36 of the hoop 20 as shown in FIG. 10 to the horizontal position 40 as shown in FIG. 2.

Figure 9:
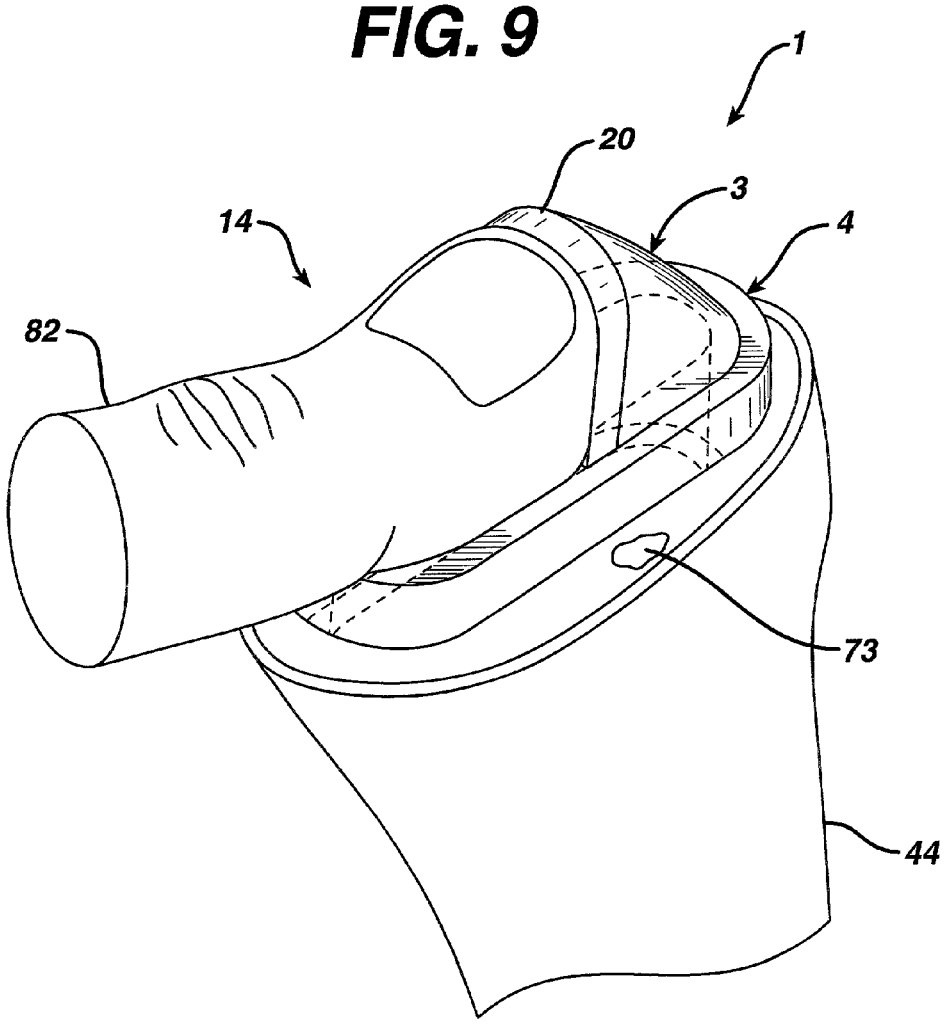
FIG. 9 is a perspective view of the pressurizer device of FIG. 1 showing the pressurizer device in position in a long bone with a thumb positioned over the opening to maintain pressure on the cement within the cavity formed in the medullary canal.

According to the present invention and referring now to FIGS. 4, 5 and 9, unlike many prior art pressurizer devices, the pressurizer device of the current invention may be retained within the opening 52 of the medullary canal 54 from the time the cement 71 is first injected in the opening 54 until the hip stem 56 is fully positioned in the opening 52 of the medullary canal 54. In fact, the pressurizer device 1 may remain in position until the cement 71 has fully cured and the hip stem 56 is permanently in position. By permitting the pressurizer device 1 to remain in position during the introduction of cement and implantation of the hip stem, the pressure of the cement may remain virtually undisturbed through the implantation procedure.

It should be appreciated that depending on the elasticity of the hood 3 and its neutral position, the pressurizer device 1 may have an opening and an avenue for the pressure to escape from the time of removal of the gun nozzle 72 to the time of insertion of the hip stem 56.

Referring now to FIG. 9, a human thumb 82 may be positioned over opening 14 of the pressurizer device 1 immediately upon the removal of the gun nozzle from the pressurizer device 1. Sufficient pressure should be applied by the thumb to overcome the patient's blood pressure to be sure that blood does not displace cement in the opening. By utilizing the technique of holding the thumb 82 over the opening 14, the time for pressure loss between the injecting of cement and the insertion of the hip stem may be in the matter of fractions of a second.

It should be appreciated that within the teachings of the present invention the pressurizer device 1 may include a hood (not shown) which extends fully over the opening (not shown) of the pressurizer device (not shown). Such a hood may include a hoop (not shown) which has a natural or relaxed horizontal position with the hood covering completely covering the opening to maintain pressure between the removal of the cement gun and the insertion of the hip stem.

Referring now to FIGS. 4 and 5, the hip stem 56 in FIG. 4 is shown partially inserted into the opening 14 of the pressurizer device 1 and partially into the opening 52 of the medullary canal 54. In this position the hoop 20 of the hood 3 is in a horizontal position but seals the cement within the canal 54.

Referring now to FIG. 5, the hip stem 56 is shown fully seated within opening 52 of the medullary canal 54. In this position the pressurizer device has its hoop 20 in the vertical position and seals the cement within the opening 52 of the medullary canal 54.

Continuing to refer to FIGS. 4 and 5, the pressurizer device 1 further serves as a centralizing device to centralize proximal section 84 of the hip stem 56 within the opening 52 of the medullary canal 54. Preferably and as shown in FIGS. 4 and 5, the sides 8 of the collar 4 have a uniform thickness TC around the collar 4 therefore centrally positioning the hip stem 56 within the opening 52.

By providing a pressurizer device which may remain in position during both the cement application and the stem insertion, a pressurizer device may be utilized which maintains pressure during substantially all of the implantation procedure.

By providing a pressurizer device including a portion of the pressurizer device which may move from a first position to a second position, a pressurizer device may be utilized which pressurizes during cement injection with a nozzle having one shape as well as during hip stem insertion with a hip stem of a different shape.

By providing a pressurizer device which remains in position during the hip stem insertion a pressurizer device may be utilized which also serves to proximally centralize the hip stem within the medullary canal.

A purpose of the present invention is to allow the introduction of PMMA bone cement into a broach femoral canal using pressurised syringe introduction. The pressurizer device allows pressurisation of the cement in the femoral cavity. The pressurizer device also allows stem introduction without removal or exchange of any of the pressurizer components. Control of the final proximal positioning of the stem in the femoral cavity is possible.

An advantage of the pressurizer device of the present invention is that pressure can be maintained on the cement from introduction of the cement through to cure without any disturbance from the pressurizer.

Although the present invention and its advantages have been described in detail, it should be understood that various changes, substitutions, and alterations could be made therein without departing from the spirit and scope of the present invention as defined by the appended claims.

What is claimed:

1. A sealing device for cooperation with a resected long bone, said device being adapted to have a first configuration for providing a seal between the resected long bone and a cement dispensing device and a second configuration for providing a seal between the resected long bone and a prosthesis component, said device comprising:
   a collar defining an opening for accommodating a prosthetic component, said collar providing a sealing surface between the sealing device and the resected long bone; and
   a hood attached to the collar, said hood and said collar providing a sealing surface between the sealing device and the cement dispensing device and a sealing surface between the sealing device and the prosthesis component.

2. A sealing device as claimed in claim 1 wherein the hood is moveable between two positions, a first position in which the hood covers at least a portion of the opening and a second position in which the opening is substantially uncovered.

3. A sealing device as claimed in claim 1:
   wherein the hood has a hoop extending across the opening in the collar; and
   wherein the hoop is attached to the collar by a sprung hinge against which it can fold laterally.

4. A sealing device as claimed in claim 1:
   wherein the hood further includes a hoop and a covering attached to the hoop; and
   wherein the covering of the hood extends from the hoop to the collar.

5. A sealing device for providing a seal between a resected long bone and a cement dispensing device during the dispensing and pressurizer of cement during implantation of a prostheses, said sealing device being adapted to permit the portion of the sealing device in contact with the resected long bone to remain in such contact during the insertion of a prosthesis component into the resected long bone, wherein said device comprises:
   a collar defining an opening for accommodating a prosthetic component, said collar providing a sealing surface between the sealing device and the resected long bone; and
   a hood attached to the collar, said hood and said collar providing a sealing surface between the sealing device and the cement dispensing device and a sealing surface between the sealing device and the prosthesis component.

6. A sealing device as claimed in claim 5 for providing a seal between a resected long bone and a cement dispensing device during the dispensing and pressurizer of cement during implantation of a prostheses, said sealing device being adapted to permit the portion of the sealing device in contact with the resected long bone to remain in such contact during the insertion of a prosthesis component into the resected long bone, wherein the hood is moveable between two positions, a first position in which the hood covers at least a portion of the opening and a second position in which the opening is substantially uncovered.

7. A sealing device as claimed in claim 5:

wherein the hood has a hoop extending across the opening in the collar; and wherein the hoop is attached to the collar by a sprung hinge against which it can fold laterally.

8. A sealing device as claimed in claim 5:

wherein the hood further includes a hoop and a covering attached to the hoop; and wherein the covering of the hood extends from the hoop to the collar.

* * * * *